United States Patent
Kerč et al.

(10) Patent No.: US 7,030,151 B2
(45) Date of Patent: *Apr. 18, 2006

(54) ATORVASTATIN CALCIUM IN A PHARMACEUTICAL FORM COMPOSITION THEREOF AND PHARMACEUTICAL FORMULATION COMPRISING ATORVASTATIN CALCIUM

(75) Inventors: Janez Kerč, Ljubljana (SI); Mateja Salobir, Ljubljana (SI); Saša Bavec, Ljubljana (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 0 days.

This patent is subject to a terminal disclaimer.

(21) Appl. No.: 10/471,906

(22) PCT Filed: Mar. 13, 2002

(86) PCT No.: PCT/IB02/00736

§ 371 (c)(1),
(2), (4) Date: Sep. 15, 2003

(87) PCT Pub. No.: WO02/072073

PCT Pub. Date: Sep. 19, 2002

(65) Prior Publication Data

US 2004/0138290 A1    Jul. 15, 2004

(30) Foreign Application Priority Data

Mar. 14, 2001    (SI)    .............................. P-200100069

(51) Int. Cl.
*A61K 209/04*    (2006.01)
*C07D 31/4035*    (2006.01)

(52) U.S. Cl. ...................... 514/422; 514/423; 548/517; 548/537

(58) Field of Classification Search ................ 548/517, 548/537; 514/422, 423
See application file for complete search history.

(56) References Cited

U.S. PATENT DOCUMENTS 5,273,995 A * 12/1993 Roth .......................... 514/422
5,686,104 A * 11/1997 Mills et al. .................. 424/451
6,121,461 A *  9/2000 McKenzie ................... 548/530
6,531,507 B1 *  3/2003 Pflaum et al. ............... 514/547
6,680,341 B1 *  1/2004 Kerc ........................... 514/547
6,696,086 B1 *  2/2004 Pflaum et al. ............... 424/464
6,806,290 B1 * 10/2004 Pflaum et al. ............... 514/547

FOREIGN PATENT DOCUMENTS

| WO | 94/16693 | 8/1994 |
| WO | 97/03958 | 2/1997 |
| WO | 97/03959 | 2/1997 |
| WO | 97/03960 | 2/1997 |
| WO | 00/35424 | 6/2000 |
| WO | 01/76566 | 10/2001 |

OTHER PUBLICATIONS

Kearney et al., "The Interconversion Kinetics, Equilibrium, and Solubilities of the Lactone and Hydroxyacid Forms of the HMG-COA Reductase Inhibitor, CI-981", Pharmaceutical Research, vol. 10, No. 10, pp. 1461-1465 (1993).

* cited by examiner

*Primary Examiner*—Kamal A. Saeed
*Assistant Examiner*—Susannah Chung
(74) *Attorney, Agent, or Firm*—John D. Thallemer

(57)    ABSTRACT

Atorvastatin calcium, the substance known by the chemical name (R—(R*,R*))-2-(4-fluorophenyl)-β, δ-dihydroxy-5-(1-methylethyl)-3-phenyl-((phenylamino)carbonyl)-1H-pyrrole-1-heptanoic acid hemi calcium salt is known as HMG-CoA reductase inhibitor and is used as an antihypercholesterolemic agent. Atorvastatin in the pharmaceutical compositions available in the market, is usually prepared as its calcium salt since it enables atorvastatin to be conveniently formulated in the pharmaceutical formulations, for example, in tablets, capsules, powders and the like for oral administration. Atorvastatin calcium can exist in an amorphous form or in one of the at least four known crystalline forms (Form I, Form II, Form III and Form IV). Atorvastatin calcium is the substance which is sparingly soluble in water, with pKa 4,5, and it has been found that the crystalline forms are less soluble than the amorphous form, which may cause problems in bioavailability of atorvastatin in the body. The present invention solves the problem of providing therapeutic equivalence of atorvastatin pharmaceutical formulation regardless the form (crystalline, amorphous, mixture of both) of atorvastatin calcium used for its preparation.

18 Claims, No Drawings

ATORVASTATIN CALCIUM IN A PHARMACEUTICAL FORM COMPOSITION THEREOF AND PHARMACEUTICAL FORMULATION COMPRISING ATORVASTATIN CALCIUM

The present invention relates to atorvastatin calcium in a novel pharmaceutical form, a novel composition comprising atorvastatin calcium, and a pharmaceutical formulation comprising said atorvastatin calcium or said composition of atorvastatin calcium. Furthermore, the present invention relates to a process for the preparation of said pharmaceutical formulation and the use of said pharmaceutical formulation comprising atorvastatin calcium as active ingredient for the treatment of hypercholesterolemia, hyperlipidemia and the like.

Atorvastatin calcium, the substance known by the chemical name (R-(R*,R*))-2-(4-fluorophenyl)-β,δ-dihydroxy-5-(1-methylethyl)-3-phenyl-((phenylamino)carbonyl)-1H-pyrrole-1-heptanoic acid hemi calcium salt is known as HMG-CoA reductase inhibitor and is used as an antihypercholesterolemic agent. Processes for the preparation of atorvastatin and key intermediates are disclosed in the U.S. Pat. Nos. 5,003,080; 5,097,045; 5,103,024; 5,124,482; 5,149,837; 5,155,251; 5,216,174; 5,245,047; 5,248,793; 5,280,126; 5,342,952 and 5,397,792. Atorvastatin in the pharmaceutical compositions available in the market, is usually prepared as its calcium salt since it enables atorvastatin to be conveniently formulated in the pharmaceutical formulations, for examples, in tablets, capsules, powders and the like for oral administration.

Atorvastatin calcium can exist in an amorphous form or in one of the at least four known crystalline forms (Form I, Form II, Form III and Form IV), which are disclosed in the patent applications WO 97/3958 and WO 97/3959. It is known that the amorphous forms of many pharmaceutical substances exhibit different dissolution characteristics and bioavailability patterns compared to the crystalline forms (Konno T., *Chem. Pharm. Bull.*, 1990; 38; 2003–2007). Bioavailability is one of the key parameters for many therapeutic indications and is dependent on the form of the substance to be used in the pharmaceutical formulation. Processes for the crystallization and the preparation, respectively, of the amorphous substance are sometimes difficult to be performed, and as a product afford amorphous-crystalline mixtures with a changeable ratio of both forms, that is, crystalline form instead of amorphous form and vice versa. Since there are differences in the solubility among individual atorvastatin forms, as the patent application WO 97/3960 particularly emphasizes, also having an indirect impact on its bioavailability, it is very important to ensure uniformity of the substance being employed in a pharmaceutical formulation. Further, in the experiment it was observed that in acidic environment all atorvastatin calcium incorporated in a pharmaceutical formulation could not be dissolved because of the poor solubility of atorvastatin calcium and preparing a pharmaceutical formulation being constantly therapeutically equivalent was rendered impossible.

The problem of uniformity of atovarstatin calcium may be solved by employing the processes in its finalization which provide constant physical characteristics of the product. The problem occurs when atorvastatin calcium of mutually variable physical characteristics from several different sources is used for the preparation of a pharmaceutical formulation. Optionally the problem can be solved by preparing atorvastatin calcium as a crystalline form only (WO 97/3958 and WO 97/3959) and an amorphous form only (WO 97/3960, WO 01/42209, and Slovene patent application P-9900271), respectively, before it is incorporated in the formulation, which requires the use of an additional operation resulting in 5 to 10% loss. Since the patient should be provided with the drug being constantly therapeutically equivalent regardless to the form of atorvastatin calcium (regarding physical characteristics) incorporated in a pharmaceutical formulation, we have decided to solve the problem of the solubility of different forms of atorvastatin calcium and consecutively its bioavailability at the level of the formulation. A further argument for this decision is the fact that atorvastatin calcium is an extremely expensive substance and all additional operations whereat a loss of the substance is possible considerably reduce the economical production process.

The patent literature describes atorvastatin calcium as an unstable substance and offers numerous solutions to provide a stable atorvastatin pharmaceutical formulation. Thus, for example, the stability of the formulation can be provided by the addition of a basic or a buffering agent to the formulation (WO 00/35425, WO 94/16603), namely by stabilizing the substance according to an analogous method described for pravastatin sodium in the patent application WO 01/93860. In order to prepare a stabilized amorphous substance, a combination of the methods disclosed in WO 01/93860, Slovene patent application P9900271, and WO 01/42209 can be used. Insofar none of the described solutions on atorvastatin pharmaceutical compositions and formulations solves the problem of uniformity of atorvastatin calcium regarding the physical parameters (crystalline and amorphous form, respectively) and associated difficulties in providing therapeutic equivalence of atorvastatin calcium pharmaceutical formulation.

An object of the present invention is to solve the problem of providing therapeutic equivalence of atorvastatin calcium in a pharmaceutical form or comprised in a composition or a pharmaceutical formulation regardless the form (crystalline, amorphous, mixture of both) of atorvastatin calcium being used for the preparation thereof. The object of the present invention also relates to a pharmaceutical formulation containing an alkalising or a buffering substance which improves the bioavailability of atorvastatin by increasing its solubility and dissolution rate in aqueous solutions.

These and further objects are accomplished by the present invention as defined in the claims.

In a first aspect of the present invention the object may be accomplished by atorvastatin calcium in a pharmaceutical form having a pH equal to or greater than the $pK_a+1$ of atorvastatin calcium.

Moreover, in a second aspect of the present invention the object may also be accomplished by a composition comprising atorvastatin calcium providing a pH equal to or greater than the the $pK_a+1$ of atorvastatin calcium to an aqueous solution thereof.

Furthermore, according to a third aspect of the present invention the above object may further be accomplished by a pharmaceutical formulation comprising atorvastatin calcium as active ingredient, wherein the pharmaceutical formulation when dissolved in a liquid aqueous medium increases the pH of said medium to a pH equal to or greater than the $pK_a+1$ of atorvastatin calcium.

Further objects of the present invention can be achieved by preferred embodiments as set forth in the dependent claims.

The features of the present invention will become more apparent from the following description of the preferred embodiments.

The inventors surprisingly found that atorvastatin calcium in a pharmaceutical form according to the present invention or a composition comprising atorvastatin capable of providing a pH equal to or greater than the $pK_a+1$ of atorvastatin calcium to an aqueous solution improves the solubility of atorvastatin calcium dissolved therein such that it is negligible whether the amorphous or the crystalline form is dissolved.

More specifically, in the experiments the applicant has found that the solubility of atorvastatin calcium in aqueous solutions is markedly improved at pH values equal to or greater than pKa+1 whereas surprisingly differences between atorvastatin calcium in crystal or amorphous form appear to be negligible. The pKa of atorvastatin's terminal carboxyl group is 4.5. Based on the above, it is preferred that when pH in the gastric microenvironment equal to or greater than pKa+1, more preferably pH of 6, is provided resulting from the composition or the pharmaceutical formulation according to the present invention comprising atorvastatin calcium, differences in the solubility will no longer be noticeable between different forms of atorvastatin calcium with different physical characteristics. The atorvastatin calcium forms having different physical characteristics which may be present in the composition or the pharmaceutical formulation according to the present invention can either be the amorphous form, the crystalline form or both forms simultaneously. Moreover, the present invention is not limited to these forms, but any physical form of atorvastatin calcium can be present in the composition or the pharmaceutical formulation of the present invention. More preferably, the amorphous atorvastatin calcium may be present in a form having a large specific surface, in particular as micronized amorphous atorvastatin calcium. Atorvastatin having a large specific surface has a further improved solubility characteristic.

In order to adjust the pH of the aqueous solution in the appropriate range, the composition or the pharmaceutical formulation according to the present invention optionally comprises a pH adjusting substance. The adjusting substance suitably used in the present invention is not specifically limited, however a substance selected from the group consisting of metal oxides, inorganic bases, organic bases, and salts of organic and inorganic acids is preferable. More preferably used pH adjusting substances are selected of the group consisting of oxides or hydroxides of alkaline or alkaline earth metals, in particular MgO, alkaline phosphate buffers, in particular $Na_3PO_4$ and $Na_2HPO_4$, and organic amines, in particular tris(hydroxymethyl)methylamine.

In the present invention, the pharmaceutical formulation when used for a single administration and comprising atorvastatin calcium as active ingredient preferably comprises the pH adjusting substance in an amount of 0.2 to 2.0 mmol, and more preferably of 0.4 to 1.2 mmol. If the pH adjusting substance is comprised in the above specific range, the pH value of 900 ml aqueous HCl solution, more generally the pH value of an simulated gastric environment of the stomach, may be properly adjusted by single administration of the pharmaceutical formulation according to the present invention. Thus, an improved solubility characteristic of the atorvastatin calcium contained in the pharmaceutical formulation can be achieved, irrespective whether the atorvastatin calcium is contained in the amorphous and/or crystalline form.

Experiments

For in vitro simulation of preferred embodiments of atorvastatin calcium pharmaceutical formulations in acidic gastric environment of the stomach according to the present invention, the dissolution testing in a simulated gastric fluid having a pH value of about pH 3, and more specifically in 900 ml of aqueous 0.001M HCl solution, was performed. The concentration of dissolved atorvastatin was then measured at 10-minute intervals.

Four different formulations were prepared in form of tablets (A1, A2, A3 and A4; their composition is shown in Table 1), which were capable of providing different pH of the aqueous solution (obtained pH values of the solutions are shown in Table 2). Measurement results of the amount of dissolved atorvastatin in % are shown in Table 3.

TABLE 1

| Composition | A1 | A2 | A3 | A4 |
|---|---|---|---|---|
| Atorvastatin amorphous, micronized* | 20.00 | 20.00 | 20.00 | 20.00 |
| Microcrystaline cellulose (Avicel PH112 or PH102)* | 98.60 | 78.60 | 72.60 | 37.10 |
| Lactose monohydrate (70–100 mesh) | 34.80 | 34.80 | 34.80 | 20.00 |
| Cross-linked carboxymethylcellulose (Ac-di-sol) | 9.60 | 9.60 | 9.60 | 9.60 |
| Polysorbate 80 | 1.30 | 1.30 | 1.30 | 1.30 |
| Hydroxypropyl cellulose (Klucel EF) | 2.00 | 2.00 | 2.00 | 2.00 |
| MgO | — | 20.00 | 26.00 | — |
| $Na_2HPO_4$ | — | — | — | 140.00 |
| Microcrystalline cellulose (Avicel PH112) | 71.90 | 71.90 | 71.90 | 48.20 |
| Cross-linked carboxymethylcellulose (Ac-di-sol) | 9.60 | 9.60 | 9.60 | 19.60 |
| Aerosil 200 | 1.20 | 1.20 | 1.20 | 1.20 |
| Mg stearate | 1.00 | 1.00 | 1.00 | 1.00 |
| TOTAL | 250.00 | 250.00 | 250.00 | 300.00 |
| Demi water for granulation | 100.00 | 70.00 | 70.00 | — |
| Ethanol refined (96%) | — | — | — | 50.00 |

*Atorvastatin in the form of calcium salt in an equivalent amount, the difference is adjusted with an amount of microcrystalline cellulose All quantities required for the preparation of one tablet are given in milligrams.

TABLE 2

|  | A1 | A2 | A3 | A4 |
|---|---|---|---|---|
| pH (1 tablet in 900 ml aqueous 0.001M HCl solution) after 15 min | 3.22 | 4.28 | 6.09 | 6.06 |
| pH (1 tablet in 900 ml aqueous 0.001M HCl solution) after 30 min | 3.21 | 4.67 | 8.88 | 6.02 |

TABLE 3

|  | A1 | A2 | A3 | A4 |
|---|---|---|---|---|
| 10 min | 56.5 | 69.7 | 74.9 | 62.2 |
| 20 min | 66.1 | 80.1 | 91.1 | 99.0 |
| 30 min | 70.6 | 85.8 | 96.3 | 97.9 |
| 40 min | 74.4 | 87.0 | 98.2 | 98.3 |
| 60 min | 75.6 | 89.6 | 99.8 | 98.8 |

As evident from the measurements, all atorvastatin was dissolved advantageously in the case if the tablet was capable to increase the pH to a value that meets atorvastatin calcium's pKa+1, more specifically the pH of 900 ml of an aqueous 0.001M HCl solution for three pH units, that is at least to pH 6. In these cases atorvastatin was dissolved at much faster rates.

In addition to improvement of the solubility, pKa+1 surprisingly also leveled the difference in solubility between atorvastatin calcium in a crystalline form and an amorphous form. To prove the above statement the granulations with the additions of different alkalising or buffering agents and different physical forms of atorvastatin calcium were prepared. Comparison of the release rate of atorvastatin from the granulations with added alkalising or buffering agents to the release rate of atorvastatin from the reference granulations with no added alkalising or buffering substances was carried out (Table 4). The pH values of solutions provided by different granulations are shown in Table 5. Measurement results of the amount of dissolved atorvastatin in % at different time intervals are shown in Table 6.

TABLE 4

| Composition | AK1 | AK2 | AK3 | AA1 | AA2 | AA3 |
|---|---|---|---|---|---|---|
| Atorvastatin crystalline* | 20.0 | 20.0 | 20.0 | — | — | — |
| Atorvastatin amorphous* | — | — | — | 20.0 | 20.0 | 20.0 |
| Microcrystalline cellulose (PH102)* | 71.3 | 71.3 | 71.3 | 71.3 | 71.3 | 71.3 |
| Lactose monohydrate (70–100 mesh) | 34.8 | 34.8 | 34.8 | 34.8 | 34.8 | 34.8 |
| Cross-linked carboxymethylcellulose (Ac-di-sol) | 9.6 | 9.6 | 9.6 | 9.6 | 9.6 | 9.6 |
| Polysorbate 80 | 2.6 | 2.6 | 2.6 | 2.6 | 2.6 | 2.6 |
| Hydroxypropyl cellulose (Klucel EF) | 2.0 | 2.0 | 2.0 | 2.0 | 2.0 | 2.0 |
| Tris | 110.0 | — | — | 110.0 | — | — |
| $Na_3PO_4$ | — | 80.0 | — | — | 80.0 | — |
| Microcrystalline cellulose (Avicel PH112) | 67.9 | 67.9 | 67.9 | 67.9 | 67.9 | 67.9 |
| Cross-linked carboxymethylcellulose (Ac-di-sol) | 9.6 | 9.6 | 9.6 | 9.6 | 9.6 | 9.6 |
| Aerosil 200 | 1.2 | 1.2 | 1.2 | 1.2 | 1.2 | 1.2 |
| Mg stearate | 1.0 | 1.0 | 1.0 | 1.0 | 1.0 | 1.0 |
| Demi water for granulation | 80.0 | 80.0 | 80.0 | 80.0 | 80.0 | 80.0 |

*Atorvastatin in the form of Ca salt in an equivalent amount, the difference is adjusted with an amount microcrystalline cellulose All quantities required for filling one capsule are given in milligrams.

TABLE 5

| | AK1 | AK2 | AK3 | AA1 | AA2 | AA3 |
|---|---|---|---|---|---|---|
| pH (1 capsule in 900 ml aqueous 0.001M HCl solution) after 15 min | 6.68 | 6.28 | 3.14 | 5.81 | 6.28 | 3.20 |
| pH (1 capsule in 900 ml aqueous 0.001M HCl solution) after 30 min | 6.95 | 6.72 | 3.15 | 5.68 | 6.30 | 3.24 |

TABLE 6

| | AK1 | AK2 | AK3 | AA1 | AA2 | AA3 |
|---|---|---|---|---|---|---|
| 10 min | 64.6 | 49.9 | 31.8 | 75.9 | 50.8 | 38.7 |
| 20 min | 76.4 | 63.4 | 44.5 | 82.6 | 62.1 | 53.4 |
| 30 min | 81.0 | 72.3 | 51.4 | 83.6 | 68.5 | 61.5 |
| 40 min | 84.2 | 77.3 | 55.8 | 83.9 | 72.8 | 66.6 |

From the obtained results it is evident that the percentage difference in the amount of dissolved amorphous and crystalline atorvastatin calcium was approximately 20% when the granulation without added alkalising or buffering substance was used, and a difference appeared minimal (<5%) when a buffering substance was added.

It was tried to additionally improve the solubility of amorphous atorvastatin calcium by enlarging the specific surface area of particles of the amorphous substance. Six different granulations were prepared in the same manner as in the previous experiment, the only difference being instead of crystalline atorvastatin, micronized amorphous atorvastatin calcium (AAM1, AAM2 and AAM3 samples) was used having several times larger specific surface area of the particles compared to nonmicronized. The pH values provided by the granulations are shown in Table 7. Measurement results of the amount of dissolved atorvastatin in % at different time intervals are shown in Table 8.

TABLE 7

| | AAM1 | AAM2 | AAM3 | AA1 | AA2 | AA3 |
|---|---|---|---|---|---|---|
| pH (1 tablet in 900 ml aqueous 0.001M HCl solution) after 15 min | 6.80 | 6.40 | 3.12 | 5.81 | 6.28 | 3.20 |
| pH (1 tablet in 900 ml aqueous 0.001M HCl solution) after 30 min | 6.76 | 6.44 | 3.30 | 5.68 | 6.30 | 3.24 |

TABLE 8

| | AAM1 | AAM2 | AAM3 | AA1 | AA2 | AA3 |
|---|---|---|---|---|---|---|
| 10 min | 85.9 | 93.9 | 41.5 | 75.9 | 50.8 | 38.7 |
| 20 min | 95.8 | 94.2 | 55.9 | 82.6 | 62.1 | 53.4 |
| 30 min | 98.4 | 93.9 | 63.8 | 83.6 | 68.5 | 61.5 |
| 40 min | 99.3 | 94.0 | 68.9 | 83.9 | 72.8 | 66.6 |

From the obtained results it is evident that there was practically no difference in the amount of dissolved amorphous and amorphous micronized atorvastatin when the granulation without added buffering agent was used, and the difference increased to more than 15–20% when a buffering agent was added.

The aforementioned experiments surprisingly showed that it was possible to provide therapeutic equivalence of atorvastatin calcium in a pharmaceutical form, a composition thereof as well as pharmaceutical formulations regardless which form (crystalline, amorphous, mixture of both) of atorvastatin calcium was used for their preparation. Of paramount importance for providing the therapeutic equivalence is the capability of the atorvastatin calcium, the composition thereof, and the pharmaceutical formulation according to the present invention to provide a pH equal to or greater than the $pK_a+1$ of atorvastatin calcium to an aqueous solution. In a preferred embodiment atorvastatin calcium, the compsoitions and the formulation of the present invention have the capability to increase the pH of 900 ml aqueous 0.001M HCl solution to pH values equal to or greater than pKa+1 or more, in particular pH 6 or more.

The other surprising finding was that the dissolved amount of micronized amorphous atorvastatin calcium in the granulation with added alkalising or buffering substance is approximately for 15% greater than in case of nonmicronized atorvastatin calcium. Here the most surprising fact is that an increase of a specific surface of the particles itself does not have an impact on the improvement of the solubility, as the solubility of micronized and nonmicronized amorphous atorvastatin calcium in the granulation with no added alkalising or buffering substance is equivalent.

The pharmaceutical formulation, which is the object of the present invention, may contain, in addition to atorvastatin calcium, one or more fillers such as microcrystalline cellulose, lactose, sugars, starches, modified starch, mannitol, sorbitol and other polyols, dextrin, dextran and maltodextran, calcium carbonate, calcium phosphate and/or hydrogen phosphate, sulfate, one or more binders such as lactose, starches, modified starch, dextrin, dextran and maltodextrin, microcrystalline cellulose, sugars, polyethylene glycols, hydroxypropyl methylcellulose, ethylcellulose, hydroxyethyl cellulose, methylcellulose, carboxy methylcellulose, sodium carboxy methylcellulose, gelatin, acacia gum, tragacanth, polyvinylpyrrolidone, magnesium aluminum silicate, one or more disintegrating agents such as cross-linked sodium carboxy methylcellulose, cross-linked polyvinylpyrrolidone, cross-linked carboxymethyl starch, starches and microcrystalline cellulose, magnesium aluminum silicate, polyacrylin potassium, one or more different glidants such as magnesium, calcium and zinc stearate, calcium behenate, sodium stearyl fumarate, talc, magnesium trisilicate, stearic acid, palmitic acid, carnauba wax, silicon dioxide, one or more buffering substances such as sodium citrate, dibasic sodium phosphate, calcium carbonate, hydrogen phosphate, phosphate, sulfate, magnesium carbonate, potassium citrate, potassium sorbate, sodium ascorbate, benzoate, hydrogen carbonate, hydrogen phosphate, or one or more basic substances such as MgO, MgOH, NaOH, $Ca(OH)_2$, tromethamine, Al Mg silicate, lauryl sulfate. If required, the formulation may also include surfactants and other conventional ingredients for solid pharmaceutical formulations such as, coloring agents, lakes, flavoring agents and adsorbents. As surfactants the following may be used: ionic surfactants such as sodium lauryl sulfate or non-ionic surfactants such as different poloxamers (polyoxyethylene and polyoxypropylene copolymers), natural or synthesized lecithins, esters of sorbitant and fatty acids (such as Span® (Atlas Chemie)), esters of polyoxyethylenesorbitan and fatty acids (such as Tween® (Atlas Chemie)), polyoxyethylated hydrogenated castor oil (such as Cremophor® (BASF)), polyoxyethylene stearates (such as Myrj® (Atlas Chemie)) or cationic surfactants such as cetyl pyridine chloride or any combination of the herein above-mentioned surfactants.

The pharmaceutical formulations of the present invention may be provided either as solid pharmaceutical formulations, such as powders, granules, tablets, or capsules, for example, or as liquid pharmaceutical formulations, preferably filled in capsules.

The solid pharmaceutical formulations according to the present invention, may be prepared as described below:

The mixture of the active ingredient, a filler, a binder, an alkalising or buffering substance, a disintegrating agent and if required a surfactant and other conventional ingredients for solid pharmaceutical formulations is homogenized employing suitable mixers, the mixture is compacted using suitable compaction machines or slugged on slugging machines, the compacts or slugs are triturated and/or sieved, fillers, disintegrating agents, buffering substances, glidants, lubricants and other conventional inactive ingredients for tablets or capsules are added, and re-homogenized. The resulting mixture is compressed into tablets or filled into capsules.

The mixture of the active ingredient, a filler, a binder, an alkalising or buffering substance, a disintegrating agent and if required a surfactant and other conventional ingredients for solid pharmaceutical formulations are homogenized employing suitable mixers, glidants and lubricants are added and re-homogenized. The resulting mixture is compressed into tablets or filled into capsules.

The mixture of the active ingredient, a filler, a binder, an alkalising or buffering substance, a disintegrating agent and if required a surfactant and other conventional ingredients for solid pharmaceutical formulations are homogenized employing suitable mixers, granulated with a suitable solvent such as water, ethanol, methanol, isopropyl alcohol, n-butyl alcohol, acetone, diethylether, ethylacetate, isopropyl acetate, methyl acetate, dichloromethane, chloroform, mixtures of these solvents such as ethanol and acetone, methanol and acetone, dichloromethane and methanol, and the mixtures thereof. The resulting granulation is dried in suitable dryers such as standard tray dryers, fluidized bed dryers, vacuum and microwave dryers, at a temperature not exceeding 60° C. To the dried granulation, glidants, disintegrating agents, alkalising or buffering substances, glidants and lubricants are added and if required other conventional ingredients for solid pharmaceutical formulations. The resulting mixture is re-homogenized and compressed into tablets or filled into capsules.

Optionally, tablets are film-coated.

The present invention is illustrated but in no way limited by the following examples.

EXAMPLES

Examples 1–2

Tablets with Added MgO or $Na_2PHO_4$

The ingredients, listed in the table below, were homogenized in a mixer and granulated with water and ethanol, respectively. The resulting granulation was dried in a vacuum dryer at a temperature not exceeding 60° C.

| Composition | A3 | A4 |
|---|---|---|
| Atorvastatin amorphous, micronized* | 20.00 | 20.00 |
| Microcrystalline cellulose (Avicel PH112 or PH102)* | 72.60 | 37.10 |
| Lactose monohydrate (70–100 mesh) | 34.80 | 20.00 |
| Cross-linked carboxymethylcellulose (Ac-di-sol) | 9.60 | 9.60 |
| Polysorbate 80 | 1.30 | 1.30 |
| Hydroxypropyl cellulose (Klucel EF) | 2.00 | 2.00 |
| MgO | 26.00 | — |
| $Na_2HPO_4$ | — | 140.00 |
| Demi water for granulation | 70.00 | — |
| Ethanol refined for granulation (96%) | — | 50.00 |

*Atorvastatin in the form of Ca salt in an equivalent amount, the difference is adjusted with an amount of microcrystalline cellulose All quantities are given in milligrams (for one tablet). The quantity of the prepared granulation was sufficient for the preparation of 1000 units of 250 mg tablets.

To the dried granulation the following was added:

| | | |
|---|---|---|
| Microcrystalline cellulose (Avicel PH112) | 71.90 | 48.20 |
| Cross-linked carboxymethylcellulose (Ac-di-sol) | 9.60 | 19.60 |
| Aerosil 200 | 1.20 | 1.20 |
| Mg stearate | 1.00 | 1.00 |

The resulting mixture was re-homogenized and compressed into tablets. The pH values provided by one tablet in 900 ml of aqueous 0.001M HCl solution were the following:

|  | A3 | A4 |
|---|---|---|
| pH (1 tablet in 900 ml aqueous 0.001M HCl solution) after 15 min | 6.09 | 6.06 |
| pH (1 tablet in 900 ml aqueous 0.001M HCl solution) after 30 min | 8.88 | 6.02 |

Examples 3–6

Capsules with Amorphous and Crystalline, Respectively, Atorvastatin Calcium with Added Tris and $Na_3PO_4$, Respectively The ingredients, listed in the table below, were homogenized in a mixer and granulated with water and ethanol, respectively. The resulting granulation was dried in a vacuum dryer at a temperature not exceeding 60° C.

| Composition | AK1 | AK2 | AA1 | AA2 |
|---|---|---|---|---|
| Atorvastatin crystalline* | 20.0 | 20.0 | — | — |
| Atorvastatin amorphous* | — | — | 20.0 | 20.0 |
| Microcrystalline cellulose (PH102)* | 71.3 | 71.3 | 71.3 | 71.3 |
| Lactose monohydrate (70–100 mesh) | 34.8 | 34.8 | 34.8 | 34.8 |
| Cross-linked carboxymethylcellulose (Ac-di-sol) | 9.6 | 9.6 | 9.6 | 9.6 |
| Polysorbate 80 | 2.6 | 2.6 | 2.6 | 2.6 |
| Hydroxypropyl cellulose (Klucel EF) | 2.0 | 2.0 | 2.0 | 2.0 |
| Tris | 110.0 | — | 110.0 | — |
| $Na_3PO_4$ | — | 80.0 | — | 80.0 |
| Demi water for granulation | 80.0 | 80.0 | 80.0 | 80.0 |

All quantities required for preparation of the granulation for one capsules are given in milligrams. The quantity of the prepared granulation was sufficient for filling 1000 capsules.

To the dried granulation the following was added:

|  | AK1 | AK2 | AA1 | AA2 |
|---|---|---|---|---|
| Microcrystalline cellulose (Avicel PH112) | 67.9 | 67.9 | 67.9 | 67.9 |
| Cross-linked carboxymethylcellulose (Ac-di-sol) | 9.6 | 9.6 | 9.6 | 9.6 |
| Aerosil 200 | 1.2 | 1.2 | 1.2 | 1.2 |
| Mg stearate | 1.0 | 1.0 | 1.0 | 1.0 |

The resulting mixture was re-homogenized and compressed into tablets. The pH values provided by one tablet in 900 ml of aqueous 0.001M HCl solution were the following:

|  | AK1 | AK2 | AA1 | AA2 |
|---|---|---|---|---|
| pH (1 tablet in 900 ml aqueous 0.001M HCl solution) after 15 min | 6.68 | 6.28 | 5.81 | 6.28 |
| pH (1 tablet in 900 ml aqueous 0.001M HCl solution) after 30 min | 6.95 | 6.72 | 5.68 | 6.30 |

Optionally, used atorvastatin could be micronized or prepared according to some other method to enlarge a specific surface area of the particles (e.g., grinding)

The invention claimed is:

1. A pharmaceutical formulation comprising atorvastatin calcium as active ingredient and a pH adjusting substance, wherein
the pharmaceutical formulation when dissolved in a liquid aqueous medium increases the pH of said medium to a pH equal to or greater than $pK_a+1$ of atorvastatin calcium.

2. The pharmaceutical formulation according to claim 1, wherein the atorvastatin calcium is present in the formulation in different physical forms.

3. The pharmaceutical formulation according to claim 2, wherein the atorvastatin calcium is present in the formulation in a crystalline and amorphous form.

4. The pharmaceutical formulation according to claim 1, wherein the atorvastatin calcium comprises amorphous atorvastatin calcium having a large specific surface of the particles.

5. The pharmaceutical formulation according to claim 4, wherein the atorvastatin calcium comprises micronized amorphous atorvastatin calcium.

6. The pharmaceutical formulation according to claim 1, wherein the atorvastatin calcium comprises crystalline atorvastatin calcium.

7. The pharmaceutical formulation according to claim 1, wherein the formulation provides in the simulated gastric fluid of pH of 3 a pH of equal to or greater than $pK_a+1$.

8. The pharmaceutical formulation according to claim 7, wherein the formulation provides a pH of 6.

9. The pharmaceutical formulation according to claim 1, wherein the amount of the pH adjusting substance is adjusted in the formulation such that a single administration increases the pH of 900 ml aqueous 0.001 M HCl solution having a pH of about 3 to a pH equal to or greater than $pK_a+1$ or more.

10. The pharmaceutical formulation according to claim 1, wherein the pH adjusting substance is contained in the pharmaceutical formulation in an amount of 0.2 to 2.0 mmol.

11. The pharmaceutical formulation according to claim 1, wherein the pH adjusting substance is selected from the group consisting of metal oxides, inorganic bases, organic bases, and salts of organic and inorganic aids.

12. The pharmaceutical formulation according to claim 11, wherein the pH adjusting substance is selected from the group consisting of metal oxides, oxides or hydroxides of the alkaline or alkaline earth metals, alkaline phosphate buffers, and organic amines.

13. The pharmaceutical formulation according to claim 1, in a form selected from the group consisting of a powder, granules, a tablet and a capsule.

14. The pharmaceutical formulation according to claim 1, comprising further one or more components selected from the group consisting of fillers, binders, buffering substances, basic substances, surfactants and other pharmaceutically acceptable ingredients.

15. The pharmaceutical formulation according to claim 10, wherein the pH adjusting substance is contained in the pharmaceutical formulation in an amount of 0.4 to 1.2 mmol.

16. The pharmaceutical formulation according to claim 12, wherein the oxide of an alkaline or akaline earth metal is MgO.

17. The pharmaceutical formulation according to claim 12, wherein the alkaline phosphate buffer is $Na_3PO_4$ or $Na_2HPO_4$.

18. The pharmaceutical formulation according to claim 12, wherein the organic amine is tris(hydroxymethyl)methylamine.

* * * * *